US009775299B2

(12) United States Patent
Zhang et al.

(10) Patent No.: US 9,775,299 B2
(45) Date of Patent: Oct. 3, 2017

(54) NONINVASIVE METHOD OF SOURCE-SINK REGULATION IN RICE

(71) Applicant: China National Rice Research Institute, Hangzhou, Zhejiang (CN)

(72) Inventors: Weixing Zhang, Hangzhou (CN); Zhiwei Zhu, Hangzhou (CN); Xiyuan Liao, Hangzhou (CN); Xihong Shen, Hangzhou (CN); Guosheng Shao, Hangzhou (CN); Jie Min, Hangzhou (CN); Weigui Zhang, Hangzhou (CN)

(73) Assignee: CHINA NATIONAL RICE RESEARCH INSTITUTE, Zhejiang (CN)

( * ) Notice: Subject to any disclaimer, the term of this patent is extended or adjusted under 35 U.S.C. 154(b) by 93 days.

(21) Appl. No.: 14/441,955

(22) PCT Filed: Sep. 24, 2013

(86) PCT No.: PCT/CN2013/084100
§ 371 (c)(1),
(2) Date: May 11, 2015

(87) PCT Pub. No.: WO2014/180088
PCT Pub. Date: Nov. 13, 2014

(65) Prior Publication Data
US 2015/0282432 A1 Oct. 8, 2015

(30) Foreign Application Priority Data
May 8, 2013 (CN) .......................... 2013 1 0166485

(51) Int. Cl.
*A01H 1/02* (2006.01)
*A01H 5/10* (2006.01)
*A01G 16/00* (2006.01)
*A01G 1/00* (2006.01)

(52) U.S. Cl.
CPC ............ *A01G 1/001* (2013.01); *A01G 16/00* (2013.01); *A01H 1/02* (2013.01)

(58) Field of Classification Search
None
See application file for complete search history.

(56) References Cited

U.S. PATENT DOCUMENTS 5,304,722 A * 4/1994 Qinxiu .................... A01H 1/02
800/303
6,294,717 B1 * 9/2001 Xie .......................... A01H 5/10
435/430

FOREIGN PATENT DOCUMENTS

CN 1085038 C 5/2002

OTHER PUBLICATIONS

Pradhan et al. Botanical Bulletin Academia Sinica 31: 217-221 (1990).*

(Continued)

*Primary Examiner* — David T Fox
(74) *Attorney, Agent, or Firm* — Wilmer Cutler Pickering Hale and Dorr LLP

(57) ABSTRACT

A noninvasive method of source-sink regulation in rice belongs to the technical field of rice production. In this method, the source-sink relationship is regulated by a rice sterile line and its identical type of maintaining line being subjected to mixed-planting and insulated pollination, or sowing and transplanting at different times and insulated pollination, so as to construct rice plant samples with gradient difference of source-sink levels. The present invention is a kind of native, natural noninvasive method of source-sink regulation, which could broaden the traditional thinking of source-sink theoretical research, especially overcome the deficiency in conventional methods such as leaf-cutting, spikelet-thinning that lead to physical injury or physiological interference. The method provides a brand new approach and solution for thoroughly investigating source-sink relationship in rice, wheat, maize and other crops, and will play an important role in enriching crop source-sink theory and also promoting the development of the related disciplines.

2 Claims, 1 Drawing Sheet

(56) References Cited

OTHER PUBLICATIONS

Jiao et al. Photosynthetica 39(2): 167-175 (2001).*
Young et al. Euphytica 51: 87-93 (1990).*
Venkateswarlu et al. Plant and Soil 47: 37-37 (1977).*
Xiao, Y. Acta Botanica Sinica 20(1): 20-25 (1978) English Abstract Only.*
Zhou et al. Zhongguo Shuidao Kexue 22(6): 590-596 (2008) Abstract Only.*
Tao et al. Zuowu Xuebao 36(10): 1796-1803 (2010) Abstract Only.*
Xu et al. Journal of Integrative Plant Biology 48(4): 440-446 (2006).*
International Search Report and Written Opinion issued by the State Intellectual Property Office of the P. R. China as International Searching Authority for International Application No. PCT/CN2013/084100 dated Feb. 20, 2014 (10 pages).
Liu et al., "Effects of Early Stage Shading on Function Leaf Growth at Grain-Filling Stage and on Grain Quality of Rice," Chinese Journal of Ecology, vol. 25, No. 10, Oct. 30, 2006 (pp. 1167-1172).
Luo, "Comparing and Observing Main Characters of Different Sources of Rice Sterile Line and Maintainer Line," Hunan Agricultural Sciences, No. 6, Dec. 27, 1981, p. 5-8.
Wang et al., "Research on Hybrid Rice Sink-Source Relationship, 1. Influence of Adjustment of Organic Nutrition on Seed Setting Characteristics," Hunan Agricultural Sciences, No. 6, Dec. 27, 1981 (5 pages), p. 1-4.
Xiang, "Comparison of an Influence on Leaf Photosynthesis Rate of Rice Male Sterile Line and Maintainer Line by Changing Source-Sink Ratio," Plant Physiology Communications, No. 5, Oct. 28, 1983, p. 37-39.

* cited by examiner

Figures

NONINVASIVE METHOD OF SOURCE-SINK REGULATION IN RICE

CROSS REFERENCE TO RELATED APPLICATIONS

This application is a National Stage Entry of PCT International Application No. PCT/CN2013/084100 filed on Sep. 24, 2013, which claims priority to Chinese Patent Application No. 201310166485.7 filed on May 8, 2013, the contents of which are incorporated herein by reference in their entirety.

TECHNICAL FIELD

The present invention belongs to the technical field of rice production, particularly relates to the noninvasive method of source-sink regulation in rice.

BACKGROUND ART

Rice production in China has experienced two breakthroughs, application of dwarf varieties in the 1950's and hybrid varieties in the 1970's, and a new breakthrough of the super rice application in recent years, which involves construction of ideal plant type, usage of hybrid vigour, physiological-ecological regulation and other various theoretical innovations and technical practices. Each yield increase and quality improvement of rice is always accompanied by the alternative improvement of the source, sink and transportation, and continuous establishment of new type of source-sink relationship. Yield and quality of rice are actually determined in the process of accumulation and transportation and distribution of photoassimilates from "source" to "sink", and depend on the intensity of source, sink and transportation as well as the interactive effects among them. Therefore, people often explore regulation methods and production technologies to achieve synchronous improvement of the yield and quality of rice from the aspect of source-sink theory.

"Source" refers to the organs that produce or output photoassimilates, such as leaves, stems and roots, among which the functional leaves and leaf sheaths are the main "source". "Sink" refers to the organs that absorb and utilize photoassimilates or other nutrients, wherein grains are the main "sink". "Transportation" refers to all transfusion tissues connecting the source and sink, currently, "transportation" is analyzed mainly from the aspects of anatomical structure of the panicle neck, the internode and the basal part of stem etc., as well as physiologically active substances. The source, sink and transportation are mutually connected and coordinated. The source provides photoassimilates to sink, the size and activity of the source affect the fullness of the grain sink; the feedback information from the sink regulates the activity of the source, the supply capacity of the source can be regulated by the needs of the sink, and the relationship between the source and sink is constantly balanced in dynamic changes; the situation of the transportation is also affected by the coordination degree of source-sink relationship to a large extent. Because of this, many physiological phenomena of source-sink relationship are still unable to be distinguished as primary or secondary, which are essentially as the result of mutual interaction between the source and sink. The effect of environmental factors and the regulation of cultivation measures affect the inner physiological and biochemical traits and apparent agriculture properties of plants by influencing the source, sink and transportation and their mutual relations during the growth and development of the plants, and the formation process of yield and quality.

Although the importance of source-sink relationship for high yield and good quality of rice is well known, no great progress has been made in the research on source-sink theory of rice until now. With the continuous development of rice production and further requirement for higher yield and better quality, the research on the source-sink relationship is unceasingly proceeding. However, there are still many problems to be further explored and solved, which is resulting from the limits of research method of the source-sink theory of crops. Generally, different ecological conditions (temperature and light, altitude, etc.) or cultivation regulation measures (density, fertilizer, etc.) are adopted to analyze the structure of source and sink and their mutual relationship among varieties, but environmental factors and cultivation measures themselves have net effect on the plant, with a reflection of "apparent source-sink relationship". To solve the problem, the plants with different source level (leaf area) or sink level (spikelet number) under the same growth conditions can be compared. However, the isogenic line with true differences at the source level and sink level is difficult to be obtained genetically. Therefore, people can only adopt the means of manual leaf-cutting, spikelet-thinning and the like, or the methods of applying mutants, inducing (inhibiting) the activity of related physiological substance and so on, to purposefully increase (decrease) the source, increase (decrease) the sink and dredge (block) the transportation. By artificially changing the source-sink relationship of the original plants, some physiological indexes might be significantly changed, which facilitates the analytical comparison with control plants, thus becoming the most commonly used technical method for investigating source-sink relationship. But many studies have shown that most of the differences generated by these methods are induced. Not only the levels of source and sink are changed by these methods, but also other functions or components are induced to change, therefore inevitably resulting in physical injury or physiological interference to the plant and changing its natural growth characteristics. Furthermore, there are artificially selective errors on leaves, grains and other organs in the practical operation; thereby the real relationship and objective rule between the source and sink fail to be reflected accurately.

In summary, in the art, it is necessary to construct experimental systems suitable for the source-sink relationship study and technology methods that are able to effectively regulate the source-sink level.

SUMMARY OF THE INVENTION

Aiming at the existing problems in the prior art, the object of the present invention is to design a noninvasive method of source-sink regulation and construct a noninvasive rice plant sample line with gradient difference of the source-sink level.

The technical solutions adopted by the present invention are as follows:

In the first aspect, the present invention provides a noninvasive method of source-sink regulation in rice, wherein the method comprises a rice sterile line and its identical type of maintaining line being subjected to mixed planting and insulated pollination.

In the second aspect, the present invention provides another noninvasive method of source-sink regulation in rice, wherein the method comprises a rice sterile line and its identical type of maintaining line being subjected to sowing and transplanting at different times and insulated pollination.

In the noninvasive method of source-sink regulation in rice of the present invention, the method may further comprise different nitrogen fertilization to different zones.

In the noninvasive method of source-sink regulation in rice of the present invention, the method may further comprise different shading-net covering to different zones.

In the noninvasive method of source-sink regulation in rice of the present invention, the rice sterile line and its identical type of maintaining line are subjected to mixed planting in a row ratio of 1:1, 2:1 or 4:2, respectively.

In the noninvasive method of source-sink regulation in rice of the present invention, the conditions for sowing and transplanting at different times are set as follows: the rice sterile line and its identical type of maintaining line sowed and transplanted at the same time, or the rice sterile line is sowed 3 days or 6 days earlier than its identical type of maintaining line and they are transplanted on the same day, respectively.

In the noninvasive method of source-sink regulation in rice of the present invention, the conditions for the nitrogen fertilization are set as follows: fertilization amounts for different zones are 0 kg/667 $m^2$, 6 kg/667 $m^2$ and 12 kg/667 $m^2$, respectively, and the fertilization is conducted according to a ratio of 5:3:2 at basal, early-tillering and panicle initiation.

In the noninvasive method of source-sink regulation in rice, the conditions of the shading-net covering are set as follows: providing no shading, 50% shading or 75% shading to different zones, respectively.

In the third aspect, the present invention provides noninvasive rice plant sample lines constructed by the noninvasive method of source-sink regulation in rice according to the first and second aspects, wherein the source-sink level exhibits gradient difference.

The beneficial effects of the present invention:

The noninvasive method of source-sink regulation in rice of the present invention is a kind of native and natural noninvasive method of source-sink regulation, which innovates the traditional thinking of source-sink theoretical research, especially overcomes the disadvantages of physical injury or physiological interference resulting from the commonly used methods, such as leaf-cutting, spikelet-thinning and the like, thus provides a brand new approach and solution for thoroughly investigating the source-sink relationship of rice, wheat, maize and other crops, and plays an important role in enriching the source-sink theory of crops and also promoting the development of the related disciplines.

DESCRIPTION OF FIGURES

Wherein: FIG. 1A shows the schematic diagram of rice growth after regulation; FIG. 1B shows the schematic diagram of rice growth without regulation.

DETAILED DESCRIPTION

Figure 1A:
FIGS. 1A and 1B are pictures demonstrating the comparison between the rice performance with source-sink regulation using the present invention and that without source-sink regulation.

Hereinafter, the present invention will be further illustrated with reference to Examples.

Example 1

In the years of 2007-2008, the inventors investigated the source-sink relationship of rice under different water conditions by the traditional methods of leaf-cutting and spikelet-thinning. It was found that physical injury and physiological interference on plant inevitably occurred in the practical operation, and there were artificial selection errors on deciding the position of leaves or grains for cutting, how to cut and the like, thereby the objective rule of the source-sink relationship is difficult to be reflected in an accurate and true way.

In order to seek a noninvasive method of the source-sink regulation without leaf cutting or spikelet cutting, the inventors utilized the sterile line and its identical type of maintaining line with only pollen fertility gene differences to construct the rice plant samples which have completely same genotype and gradiently different seed setting rate (sink level), basing on the production theory and technology of basic seeds of three lines of hybrid rice. Furthermore, in the years of 2009-2010, four groups of sterile line and its identical type of maintaining line (Zhong 9A/Zhong 9B, You 1A/You 1B, II-32A/II-32B, and Qianjiang 1A/Qianjiang 1 B) were used as materials. Under field conditions, the sterile lines and their maintaining lines were subjected to downwind (wind direction in flowering period) side-by-side planting, mixed-planting with different row ratios (A/B row ratio of 1:1, 2:1, 4:2, 6:2), or sowing and transplanting at different times and mixed-planting (A and B were transplanted at the same time, and A was sowed 3 days, 6 days, or 9 days earlier than B but they were transplanted on the same day), respectively, and plastic film was used for insulated pollination. Under the pot culture conditions, pots were filled with soil, in which 6 plants of sterile lines VS 3 plants of maintaining lines were subjected to mixed-planting and insulated pollination. Different pollen amounts were provided by the maintaining lines to the sterile lines for pollination. Each treated sterile line and its maintaining line sowed and transplanted at the same time were harvested for examination. Total spikelet number per plant, total spikelet number and filled spikelet number per panicle were examined, weight of 1000-grain was measured, and seed setting rate, potential capacity (total spikelet number×filled spikelet weight) and practical capacity (total spikelet number×seed setting rate×filled spikelet weight) were calculated to analyze the difference in sink level between rice plant samples.

The results indicated that, when the sterile line and its identical type of maintaining line were subjected to side-by-side planting along the wind direction in flowering period or subjected to mixed-planting in different ratios of row number (or plant number), or the sterile line was subjected to sowing 3-9 days earlier than its identical type of maintaining line and mixed-planting, there were differences in seed setting rate due to the difference of pollen amount provided by the maintaining line to the sterile line. Further investigation demonstrated that, for the sterile line plant with basically consistent photosynthetic leaf area and the total spikelet number before pollination, because the seed setting rates were different after pollination, there were significant difference in the green leaf duration in the grain filling period, leaf photosynthetic rate and grain plumpness, thus source-sink relationship also changed obviously. Accordingly, the inventors had designed a noninvasive method of source-sink regulation to construct different sink level differences by reasonably mixed-planting at different times and separately pollinating the sterile line and its maintaining line.

Figure 1B:

The rice sterile line has normal pistil but its stamen pollen is abortive, thus it can not self-fertilize and seed setting. It can fruit and reproduce normally after pollination by its identical type of maintaining line, and its fertility is controlled by genes. Meanwhile, the development of the pistil and stamen of the maintaining line is normal so that it can self-fertilize and set seed. It is only different from the sterile line in terms of pollen fertility. Essentially, they are a pair of allelic gene lines. After the sterile line and the maintaining line are subjected to reasonable mixed-planting, sowing at different times and insulated pollination, or the maintaining line is planted at one side of the sterile line and natural wind is utilized for pollination to allow the maintaining line to provide different amounts of pollen to the sterile line for pollination, sterile line rice plants with different seed setting rate are obtained. Therefore, the sterile line rice plants with different seed setting rate, together with unpollinated sterile line rice plants and normally seed setting maintaining line rice plants, constitute rice plant sample lines having gradiently different seed setting rate, which have completely the same genotype. Regarding the unpollinated sterile line plants as the lowest sink level and its identical type of maintaining line plants as the highest sink level, the rice plant samples with different sink levels are formed (see FIG. 1). Before pollination, photosynthetic source level and potential sink capacity of different rice plant sample lines are identical, but after pollination and the accompanying fusion of sperm and egg, and the growth of rice, different sink strength gradients and sink activity levels are formed. Due to the feedback regulation of sink on source, different sink level and the corresponding source-sink relationship will be formed subsequently. If it is assisted with source-sink treatment with different nitrogen application or source reducing treatment with different degrees of shading, the rice plant sample lines with gradient difference in source-sink level can be constructed.

Example 2

1. Materials and Methods:

The following example was carried out in Fuyang experimental site of China National Rice Research Institute (CNRRI) in 2011. The soil conditions in the experimental field were as follows: pH 5.76, organic matter 36.7 g/kg, total nitrogen 2.03 g/kg, total phosphorus 1.03 g/kg, total potassium 22.4 g/kg, alkali hydrolyzable nitrogen 155 mg/kg, available phosphorus 7.9 mg/kg, and available potassium 64.8 mg/kg. The sink regulation method of Example 1 was adopted. A group of sterile line and its maintaining line (Zhong 9A/Zhong 9B) were selected as testing materials. A and B were alternately planted (1:1, 2:1 or 4:2 row ratio) in such ways that A and B were subjected to sowing and transplanting at the same time, A was subjected to sowing 3 days or 6 days earlier than B and they were transplanted on the same day, respectively. Treatments were arranged in a split-plot design with nitrogen application or shading treatments as main plots and test materials as sub-plots. The experiment was replicated 3 times and sub-plot size was 5.4 $m^2$. Three nitrogen application rates were implemented as follows: 0 kg/667 $m^2$ (N0), 6 kg/667 $m^2$ (N6) and 12 kg/667 $m^2$ (N12). The nitrogen fertilizer was applied in three splits (50% as basal, 30% at early-tillering, 20% at panicle initiation). The ratio of N:P:K was 1:0.5:0.5. All phosphate fertilizer was applied as basal. The potassium fertilizer was split equally at basal and early-tillering. Three shading treatments were provided as follows: no shading (CK), 50% shading and 75% shading (covering with different degrees of shading-nets; shading period was from heading to maturity), and fertilization management was the same with the N12 treatment. Seedlings were raised on a wet seedbed. Seeds were sown on May $25^{th}$, and seedling received 5 kg/667 $m^2$ of urea at two to three leaves stage. Twenty-day-old seedlings were transplanted on June $15^{th}$. Transplanting was done at a hill spacing of 20.0 cm×20.0 cm with two seedlings per hill. Each field operation such as sowing, transplanting seedlings, fertilizing, spraying pesticide, etc. was finished within the same day for all treatments. The fertilizers were quantified for each plot to achieve uniformity. At full heading stage and 20 days after flowering, green leaf area of the whole plant and dry weight of each organ such as leaf, stem and sheath, or panicle were measured. At maturity stage, grain yield and yield components were determined. Source levels and sink levels and their mutual relationship were analyzed for each treatment.

2 Results and Analysis:

The results of variance analysis demonstrated that tiller number per plant, effective panicle number per plant, the spikelet number per panicle, seed setting rate, 1000-grain weight, harvested yield, theoretical yield and other agronomy characteristics with the method of the non-invasive regulation of source-sink provided in the present invention were significantly different between mixed-planting treatments of different experimental materials. The differences were dependent on nitrogen fertilizer levels and there was an obvious difference between nitrogen application and no nitrogen application. As shown in Table 1, compared with the maintaining line Zhong 9B subjected to sowing and transplanting at the same time, the sterile line Zhong 9A showed 51.5% and 92.6% decline in seed setting rate, respectively, by sowing the maintaining lines 3 days and 6 days later to pollinate the sterile line. The results indicate that the practical sink level also can be significantly reduced without cutting spikelet. At the same time, because source supply was excessive, branched panicles in the sterile line plant were newly developed on the basis of original tiller, resulting in effective panicle numbers increasing significantly but the filled spikelet numbers decreasing significantly, thereby the final grain yield decreases significantly, however, the original source-sink relationship was completely broken and non-invasive regulation of source-sink was realized.

TABLE 1

Effect of noninvasive method of source-sink regulation on the properties of seed setting rate and yield

| Source-Sink treatments | Tiller number per plant | Effective panicle per plant | Spikelet number per panicle | Seed setting percentage (%) | Weight of 1000-grain (g) | Harvested yield (kg/667 $m^2$) | Theoretical yield (kg/667 $m^2$) |
|---|---|---|---|---|---|---|---|
| Zhong 9B | 12.4 ab | 12.4 c | 115.5 a | 79.4 a | 22.54 b | 380.78 a | 428.44 a |
| N0 | 11.0 b | 11.0 b | 107.9 b | 80.9 a | 22.42 a | 341.90 b | 358.44 b |
| N6 | 13.1 a | 13.1 a | 117.9 ab | 78.6 a | 22.53 a | 386.34 ab | 456.19 a |
| N12 | 13.0 a | 13.0 a | 120.8 a | 78.9 a | 22.68 a | 414.12 a | 470.67 a |
| Zhong 9A/B3 | 12.1 b | 14.3 b | 113.8 a | 38.5 b | 23.19 a | 223.84 b | 242.08 b |

TABLE 1-continued

| Effect of noninvasive method of source-sink regulation on the properties of seed setting rate and yield | | | | | | | |
|---|---|---|---|---|---|---|---|
| Source-Sink treatments | Tiller number per plant | Effective panicle per plant | Spikelet number per panicle | Seed setting percentage (%) | Weight of 1000-grain (g) | Harvested yield (kg/667 $m^2$) | Theoretical yield (kg/667 $m^2$) |
| N0 | 10.9 c | 14.2 a | 108.0 a | 42.6 a | 23.50 a | 211.13 a | 255.24 a |
| N6 | 11.9 b | 13.9 a | 115.7 a | 37.6 ab | 23.27 a | 232.71 a | 237.52 a |
| N12 | 13.6 a | 14.8 a | 117.8 a | 35.3 b | 22.80 b | 227.69 a | 233.50 a |
| Zhong 9A/B6 | 12.8 a | 26.0 a | 108.7 b | 5.9 c | 23.41 a | 72.27 c | 64.84 c |
| N0 | 11.3 b | 22.6 c | 107.9 a | 6.2 a | 23.50 a | 63.34 b | 58.63 a |
| N6 | 12.9 a | 26.5 b | 105.9 a | 7.1 a | 23.50 a | 80.67 a | 77.77 a |
| N12 | 14.0 a | 28.9 a | 112.3 a | 4.6 a | 23.24 a | 72.78 ab | 58.13 a |

The inventors state that the present invention employs the embodiments above to describe the detailed structural feature and method of the present invention, but the present invention is not limited to the detailed structural feature and method above, i.e. it does not mean that the present invention must rely on the detailed structural feature and method above to be implemented. Persons skilled in the art should understand, any improvement of the present invention, the equivalent replacement of the raw materials of the present invention product, adding auxiliary ingredients, specific mode selection, etc. all fall within the protection scope and disclosure scope of the present invention.

The invention claimed is:

1. A noninvasive method of source-sink regulation in rice to construct different sink level differences, wherein the method comprises:

subjecting a rice sterile line (A) and its identical type of maintaining line (B) to mixed planting in a sterile: maintaining row ratio of 1:1, 2:1 or 4:2 or in a sterile: maintaining plant ratio of 6:3, sowing and transplanting, and insulated pollination;

wherein the sowing and transplanting comprise the sterile line (A) being sowed 3 days, 6 days, or 9 days earlier than its identical type of maintaining line (B), and the sterile line and its identical type of maintaining line being transplanted on the same day; and wherein the rice sterile line and its identical type of maintaining line are selected from the group consisting of Zhong 9A/Zhong 9B and II-32A/II-32B.

2. A noninvasive method of source-sink regulation in rice to construct different sink level differences of claim 1, wherein a plastic film is used for the insulated pollination.

* * * * *